US008485978B2

(12) United States Patent
Linder

(10) Patent No.: US 8,485,978 B2
(45) Date of Patent: Jul. 16, 2013

(54) SYSTEMS AND METHODS FOR NONINVASIVELY MONITORING BAROREFLEX RESPONSE AND NOMINAL BLOOD VOLUME

(75) Inventor: Stephen Paul Linder, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1916 days.

(21) Appl. No.: 11/624,065

(22) Filed: Jan. 17, 2007

(65) Prior Publication Data
US 2007/0213619 A1    Sep. 13, 2007

Related U.S. Application Data

(60) Provisional application No. 60/760,042, filed on Jan. 17, 2006, provisional application No. 60/815,360, filed on Jun. 21, 2006.

(51) Int. Cl.
A61B 5/02    (2006.01)

(52) U.S. Cl.
USPC .................................................. 600/481

(58) Field of Classification Search
USPC ................................ 600/481, 485, 500
See application file for complete search history.

(56) References Cited

U.S. PATENT DOCUMENTS

2005/0272984 A1* 12/2005 Huiku ........................ 600/301

OTHER PUBLICATIONS

Linder, S.P. et al. "Using the Morphology of Photoplethysmogram Peaks to Detect Changes in Posture" Journal of Clinical Monitoring and Computing vol. 20 No. 3 2006, pp. 151-158.
Linder, S.P. et al. "Using the Morphology of the Photoplethysmogram Envelope to Automatically Detect Hypovolemia" Proc. of the 19th IEEE Symposium on Computer-Based Medical Systems 2006, 6 pages.
Linder, S.P. et al. "Using PPG Morphology to Detect Blood Sequestration" (2006), Dartmouth College. Hanover, NH, USA, 2 pages.
Chang, J.M. et al., "Investigating respiratory variation using a forehead reflectance pulse oximeter to identify airway obstruction for automated remote triage" Bioengineering Conf. 2005. Proc. of the IEEE 31st Annual Northeast (2005), pp. 244-245.
Chang, J. et al., "Investigating respiratory variation in the plethysmograph to identify obstructive sleep apnea" 2005, Dartmouth College. Hanover, NH, USA, 1 page.
Cooke, W.H. et al. "Heart Rate Variability and Spontaneous Baroreflex Sequences: Implications for Autonomic Monitoring During Hemorrhage" The Journal of TRAUMA[ Injury, Infection, and Critical Care, Apr. 2005, vol. 58, No. 4, p. 798-805.
Knorr, B.R., et al. "Using a Generalized Neural Network to Identify Airway Obstructions in Anesthetized Patients Post-Operatively based on Photoplethysmography" Proc. of the 28th IEEE, EMBS Annual International Conference, New York City, USA, Aug. 30-Sep. 3, 2006, pp. 6765-6768.

(Continued)

*Primary Examiner* — Patricia Mallari
*Assistant Examiner* — Christian Jang
(74) *Attorney, Agent, or Firm* — Lathrop & Gage LLP

(57) ABSTRACT

Systems and methods for noninvasively monitoring baroreflex response and nominal blood volume are disclosed herein. Software and methods for evaluating morphological features of a photoplethysmogram (PPG) obtained using a pulse oximeter allow for the affirmative detection and quantification of the baroreflex response from data obtained during orthostatic stress tests, lower body negative pressure chamber tests and treadmill stress tests.

8 Claims, 13 Drawing Sheets

OTHER PUBLICATIONS

Knorr, B.R., et al. "Using Neural Networks to Identify Airway Obstructions in Anesthetized Patients based on Photoplethysmography" 2006 IEEE, pp. 193-194.

Knorr-Chung, B.R., et al. "Identifying Airway Obstructions Using Photoplethysmography (PPG)" J. Clinical Monitoring and Computing (2008) 22:95-101.

Wendelken, S.M. et al., "Using a Forehead Reflectance Pulse Oximeter to Detect Changes in Sympatheric Tone" Proc. 26th Annual Int'l Conf. of the IEEE EMBS Sep. 2004, pp. 325-328.

Wendelken, S.M. "Using a Forehead Reflectance Pulse Oximeter to Detect Changes in Sympathetic Tone" Thesis, Thayer School of Engineering, Dartmouth College, May 2004, 108 pages.

* cited by examiner

SYSTEMS AND METHODS FOR NONINVASIVELY MONITORING BAROREFLEX RESPONSE AND NOMINAL BLOOD VOLUME

RELATED APPLICATIONS

This application claims the benefit of priority to U.S. Application Nos. 60/760,042, filed Jan. 17, 2006, and 60/815,360, filed Jun. 21, 2006, each of which is incorporated herein by reference.

U.S. GOVERNMENT RIGHTS

This invention was made with Government support under grant 2000-DT-CX-K001 awarded by the Department of Homeland Security, Science and Technology Directorate, and grant 2005-DD-BX-1091 awarded by the Bureau of Justice Assistance, United States Department of Justice. The Government has certain rights in this invention.

BACKGROUND

The baroreflex regulates blood pressure through specialized nerve cells called baroreceptors that sense increases or decreases in blood pressure. Baroreceptors send signals to the brain that indicate whether heart rate and vascular tone (i.e., constriction of arterioles and veins in the peripheral vascular system) should be increased, decreased or kept constant in response to changes in blood pressure. For example, when a person stands from a seated or supine position, gravity forces blood to pool in the lower extremities. Blood pressure drops momentarily while signals from baroreceptors are received and processed by the brainstem, which increases heart rate and vascular tone to reestablish a nominal blood pressure. If the body does not properly compensate for the shift in blood volume, known as orthostatic hypotension, a person may experience syncope (i.e., fainting, passing out).

It is important for a medical practitioner evaluating a patient who has suffered a syncopal episode to determine the cause of the episode, so that the patient may be properly treated. For example, syncope may be caused by an inadequate baroreflex due to emotional stress, pain, shock, orthostatic stress, overheating, dehydration, exhaustion, violent coughing spells, medications and other drugs (e.g., beta-blockers, alcohol), and adrenal insufficiency, as well as a wide variety of cardiac, neurologic, psychiatric, metabolic and lung disorders. Initial treatment for an inadequate baroreflex is administration of intravenous fluids to increase blood volume. However, administration of fluids may be improper when syncope is caused by a non-baroreflex related event, such as edema or congestive heart failure.

To distinguish between baroreflex and non-baroreflex related events, a patient's "orthostatics" are measured. In a typical measurement, a patient lies flat for approximately five minutes. Basal blood pressure and pulse are obtained in this supine position. The patient is then asked to sit with feet dangling or to stand, and their blood pressure and pulse are taken a second time. The patient may remain sitting or standing for a minute or two and blood pressure and pulse may be taken a third time. When a patient is incoherent or unable to sit or stand unaided, the patient may be secured to a tilt-table for the purpose of performing the orthostatic stress test. A sustained increase in pulse of twenty beats per minute or a decreased systolic pressure of more than 20 mmHg is considered a positive indication of an inadequate baroreflex.

Orthostatic measurements are designed to detect the absence of a sufficient baroreflex (i.e., to test a null hypothesis), and they may be inaccurate if blood pressure and pulse measurements are taken too slowly. The measurements are thus subject to human error and variation among practitioners. In the absence of objective and affirmative data showing the presence of a physiological response, practitioners frequently request additional and often expensive tests, such as electroencephalography (EEG), magnetic resonance (MR) or computed tomography (CAT) brain scans, and electrocardiography (EKG) during workup of syncopal episodes.

In the above mentioned orthostatic test, the patient's pulse may be monitored using a pulse oximeter, which is an optical device that attaches to a patient's finger, ear or other thinly skinned body part, to measure blood oxygen saturation and pulsatile flow (i.e., heart rate). The pulse oximeter shines two colors of light onto the skin that are absorbed differently by hemoglobin in the blood depending on whether the hemoglobin is oxygenated or deoxygenated. The amount of light absorption is used to calculate the percentage of oxygenated hemoglobin in the blood (i.e., blood oxygen saturation). A photoplethysmogram (PPG) can be generated by measuring the change in light absorption caused by volumetric changes within the perfused skin.

Volumetric changes in skin perfusion result from a combination of cardiac and respiratory pressure effects, as well as vascular resistance of the skin. Cardiac pressure, which varies as the heart contracts and expands with each heartbeat, is attenuated by respiration which varies intrapleural pressure, i.e., the pressure between the thoracic wall and the lungs. This respiratory effect is often referred to as Respiratory Induced Variation (RIV). During inspiration, intrapleural pressure decreases by up to 4 mmHg, which distends the right atrium, allowing for faster filling and increased stroke volume. This increased stroke volume means that more blood leaves the venous pool and is accommodated in the central pool. Conversely, during exhalation, the heart is compressed, decreasing cardiac efficiency and reducing stroke volume. Blood from the central pool is forced into the venous plexus. RIVs vary between individuals and each individual's RIV varies with the tidal volume of each respiration.

Analysis of PPG data for the types of features discussed above has historically been performed using frequency-domain or time-domain signal processing techniques. Frequency-domain techniques provide average values of features, such as average heart rate, while time-domain techniques allow for the extraction of features such as pulse height and instantaneous heart rate. Additionally, an RIV may be plotted by connecting one point (e.g., the peak or valley) from each of a series of cardiac pulses to create an envelope, i.e., a curve tangent to each of a family of curves or lines. The observed RIV envelope rises and falls with a frequency corresponding to respiratory rate rather than heart rate.

SUMMARY

In one embodiment, a software product includes instructions, stored on computer-readable media, wherein the instructions, when executed by a computer, perform steps for detecting the presence of a baroreflex response, including instructions for obtaining photoplethysmographic (PPG) data; instructions for determining one or more of the following parameters: (a) a normalized peak width of each cardiac cycle, (b) an amplitude of the pulsatile component of each cardiac cycle in the PPG data derived from an ear sensor, and (c) an instantaneous pulse rate; instructions for determining a median value for the one or more parameters using a representative sample of cardiac cycles; and instructions for providing a result indicative of the presence of the baroreflex response when one or more of the following is observed: (d) an increase in the normalized peak width of 5% or more relative to the median normalized peak width, (e) a two-fold decrease in the amplitude of the pulsatile component relative to the median pulsatile amplitude, and (f) an increase in the instantaneous pulse rate of at least 20% relative to the median pulse rate.

In one embodiment, a software product includes instructions, stored on computer-readable media, wherein the instructions, when executed by a computer, perform steps for detecting the presence of a baroreflex response, including instructions for obtaining photoplethysmographic (PPG) data; instructions for determining a normalized peak width of each cardiac cycle; instructions for determining a median normalized peak width using a representative sample of cardiac cycles; and instructions for providing a result indicative of the presence of the baroreflex response when an increase in the normalized peak width of 5% or more relative to the median normalized peak width is detected.

In one embodiment, a method of detecting the presence of a baroreflex response includes obtaining photoplethysmographic (PPG) data; and detecting one or more of the following: (a) an increase in a normalized peak width of 5% or more relative to a median normalized peak width, (b) a two-fold decrease in an amplitude of a pulsatile component relative to a median pulsatile amplitude of the PPG data derived from an ear sensor, (c) an increase in an instantaneous pulse rate of at least 20% relative to a median pulse rate, (d) a height of a top RIV envelope that is greater than a difference between a minimum value of the top RIV envelope and a maximum value of a bottom RIV envelope, (e) a synchronous rise of a top RIV envelope and a bottom RIV envelope by a significant proportion of a peak amplitude, (f) a synchronous fall of a top RIV envelope and a bottom RIV envelope by a significant proportion of a peak amplitude, and (g) a PPG spindle wave.

In one embodiment, a method of quantifying a baroreflex response includes: obtaining photoplethysmographic (PPG) data; determining an instantaneous value and a sustained value for one or more of the following parameters: (a) a normalized peak width of each cardiac cycle; (b) an amplitude of the pulsatile component of each cardiac cycle in the PPG data derived from an ear sensor; and (c) an instantaneous pulse rate; determining a ratio of the instantaneous value to the sustained value for one or more of (a), (b) and (c); and comparing the ratio to a library of known ratios.

In one embodiment, a software product includes instructions, stored on computer-readable media, wherein the instructions, when executed by a computer, perform steps for detecting the presence of a baroreflex response, including instructions for obtaining photoplethysmographic (PPG) data; instructions for determining one or more of the following parameters: (a) a normalized peak width of each cardiac cycle; (b) an amplitude of the pulsatile component of each cardiac cycle in the PPG data derived from an ear sensor; and (c) an instantaneous pulse rate; instructions for determining a median value for the one or more parameters using a representative sample of cardiac cycles; and instructions for providing a result indicative of the presence of the baroreflex response when a statistically significant change in the median value is detected using a statistical threshold of p<0.01.

DETAILED DESCRIPTION

Figure 1:
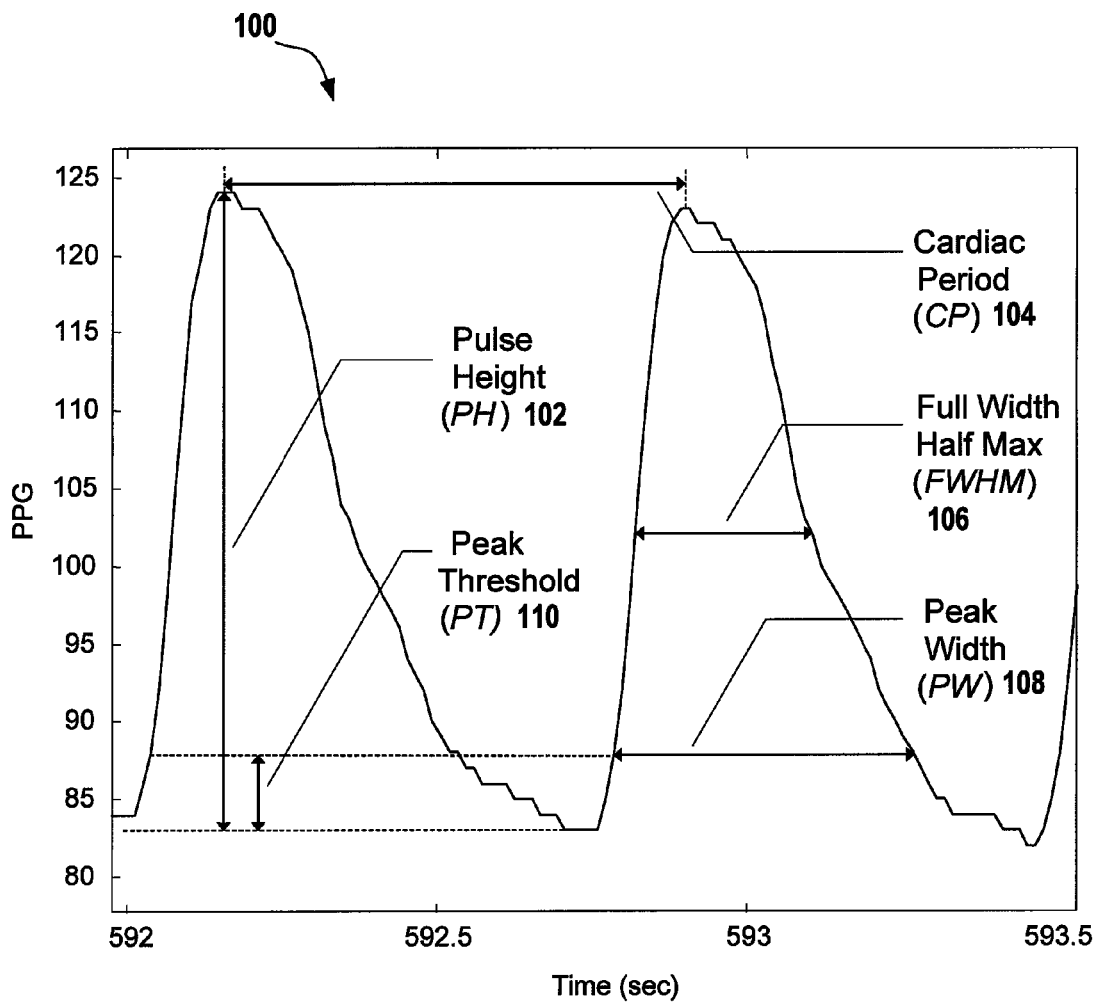
FIG. 1 shows cardiac features of a photoplethysmogram (PPG).

The instrumentalities described herein provide noninvasive systems and methods for monitoring baroreflex response and nominal blood volume. Such systems may, for example, be used by emergency personnel to distinguish between baroreflex and non-baroreflex related events, by athletes to monitor blood volume loss due to excessive perspiration, by healthcare providers to monitor a patient's fluid loss, and by surgeons to detect hemorrhaging. They may also be used to monitor physical stress in astronauts, firefighters, athletes and patients with advanced cardiac disease to provide advanced warning of an impending cardiac episode.

As used herein, a "representative sample" is a sample size that is large enough for statistically significant comparisons to be made against the representative sample. In one example, a representative sample is about thirty to forty cardiac cycles.

As used herein, the term "instantaneous" refers to a short, non-statistically significant observation period. For example, an instantaneous pulse rate may refer to an observation period of five consecutive cardiac cycles, usually occurring in 2-7 seconds.

A computer software product is a machine readable device having recorded thereon a sequence of machine readable instructions for instructing a machine to perform specific tasks. The sequence of instructions may, for example, be recorded in media such as a CD, DVD, magnetic tape, or magnetic disk, or memory such as EEPROM, ROM, or RAM circuitry. A machine having an embedded microprocessor with firmware or software embedded in an EEPROM or ROM therefore includes a computer software product.

As used herein, the "presence of a baroreflex response" refers to the physiological response to a change in blood pressure that is expected for a normal, healthy subject. A change in blood pressure may, for example, result from blood hemorrhaging or from blood sequestration due to orthostatic stress, either of which may present as an absence of a baroreflex response. In one embodiment, the presence of a baroreflex response may be detected, using PPG data, as one or more of the following: (a) an increase in a normalized peak width of a cardiac cycle in the PPG of 5% or more relative to a median normalized peak width, (b) a two-fold decrease in an amplitude of a pulsatile component of a cardiac cycle from PPG data derived from an ear sensor relative to a median pulsatile amplitude of the PPG data derived from the ear sensor, (c) an increase in an instantaneous pulse rate of at least 20% relative to a median pulse rate, (d) a height of a top RIV envelope that is greater than a difference between a minimum value of the top RIV envelope and a maximum value of a bottom RIV envelope, (e) a synchronous rise of a top RIV envelope and a bottom RIV envelope by a significant proportion of a peak amplitude, (f) a synchronous fall of a top RIV envelope and a bottom RIV envelope by a significant proportion of a peak amplitude, and (g) a PPG spindle wave. The presence of a baroreflex response may also be detected, using PPG data, as a statistically significant change in the median value of normalized peak width, peak height, pulse rate or another parameter, using a statistical threshold of $p<0.01$. The "absence of detection of a baroreflex response" indicates that the baroreflex response is either completely lacking, such as occurs during failure of autonomic responses, or below a detectable level. A baroreflex response that is below a detectable level may be caused, for example, by low blood volume. Thus, the present systems and methods provide for detection of a nominal blood volume.

Upon reading and fully understanding this disclosure, it will be appreciated by those skilled in the art that the instantaneous pulse rate of a normal, healthy individual will rise in response to orthostatic stress, and then the pulse rate will rapidly return to a basal level as arterioles and veins in the peripheral vascular system constrict. In subjects having an inadequate baroreflex, the pulse rate does not rapidly return to a basal level and the increased pulse rate is sustained. A "sustained" pulse rate may, for example, be detected by binning data following the prompt to sit or stand in an orthostatic test. The first bin would include data for the instantaneous pulse rate. One or more successive bins may be compared to the median pulse rate to determine whether or not the elevated pulse rate is sustained.

In one embodiment, the ratio of the instantaneous pulse rate to a sustained pulse rate may provide a quantitative measure of the baroreflex response. Likewise, the ratio of an instantaneous normalized peak width to a sustained normalized peak width, and the ratio of an instantaneous amplitude of the pulsatile component to a sustained amplitude of the pulsatile component may provide a quantitative measure of the baroreflex response. Comparative libraries of such ratios may be compiled and used to quantify the baroreflex response. Quantification of the baroreflex response may allow for the diagnosis and treatment of various conditions.

In one embodiment, systems and methods for evaluation of recent syncopal episodes are provided. These systems and methods allow for the affirmative detection of physiological changes associated with the baroreflex, so that it is possible to distinguish between baroreflex related and non-baroreflex related syncopal events.

In one embodiment, systems and methods for evaluation of beta-blocker dosage and effects are provided. Beta-blockers are a class of drugs used to lower heart rate and reduce blood pressure. They also prevent the release of renin, a hormone produced by the kidneys that constricts blood vessels. Thus beta-blockers may alter a person's normal baroreflex, such that an excessive dose can lead to an inadequate baroreflex and syncopal episodes.

In one embodiment, systems and methods for evaluation of hypovolemic shock and dehydration are provided. Hypovolemic shock is the failure of circulation due to low blood volume, which may result from bleeding during injury or dehydration. Further, heat stroke and heat exhaustion involve dehydration. All of these conditions may be diagnosed by the systems and methods described herein.

In one embodiment, systems and methods for regulation of treatment of congestive heart failure are provided. Congestive heart failure is usually treated by drawing off excess fluid from a patient, usually by administering large doses of diuretics, most commonly loop diuretics such as Lasix® (trademark of Aventis Pharma Deutschland Gmbh, Frankfurt, Germany for furosemide). However, it is difficult to determine how much excess fluid a patient is carrying, and improper dosing of diuretics, or continued dosing with concomitant vomiting or diarrhea, can lead to dehydration and hypovolemic shock. The systems and methods described herein may be used to regulate the dosage and timing of diuretic administration. For example, baroreflex response, and thus nominal blood volume, may be monitored periodically via orthostatic stress tests to insure that a patient is not becoming dehydrated. In this way, administration of diuretics may be used to drain fluid from, or prevent reaccumulation of fluid in, the patient's lungs, without leading to kidney damage or syncopal episodes.

FIG. 1 shows cardiac features of a photoplethysmogram (PPG) 100. The features of interest include pulse height (PH) 102, cardiac period (CP) 104, full width half maximum (FWHM) 106, peak width (PW) 108, peak threshold (PT) 110, and normalized peak width (NPW). Pulse height 102 is the difference between the maximum of a cardiac cycle and the previous minimum, where a cardiac cycle is represented as a single peak. Cardiac period 104 is the difference in time between the peaks of two consecutive cardiac cycles. Full width half maximum 106 is the width of the peak at half the maximum value of the cardiac amplitude. Peak width 108 is the width of the peak at a predetermined peak threshold 110. Normalized peak width is the PW 108 divided by the CP 104. The systems and methods described herein involve the extraction of data related to the shape of individual cardiac pulses. Whereas frequency-domain techniques may be used to analyze stationary processes, analyzing the changes in morphology between individual cardiac cycles provides for the detection and characterization of dynamic changes in the cardiovascular system.

Figure 2:
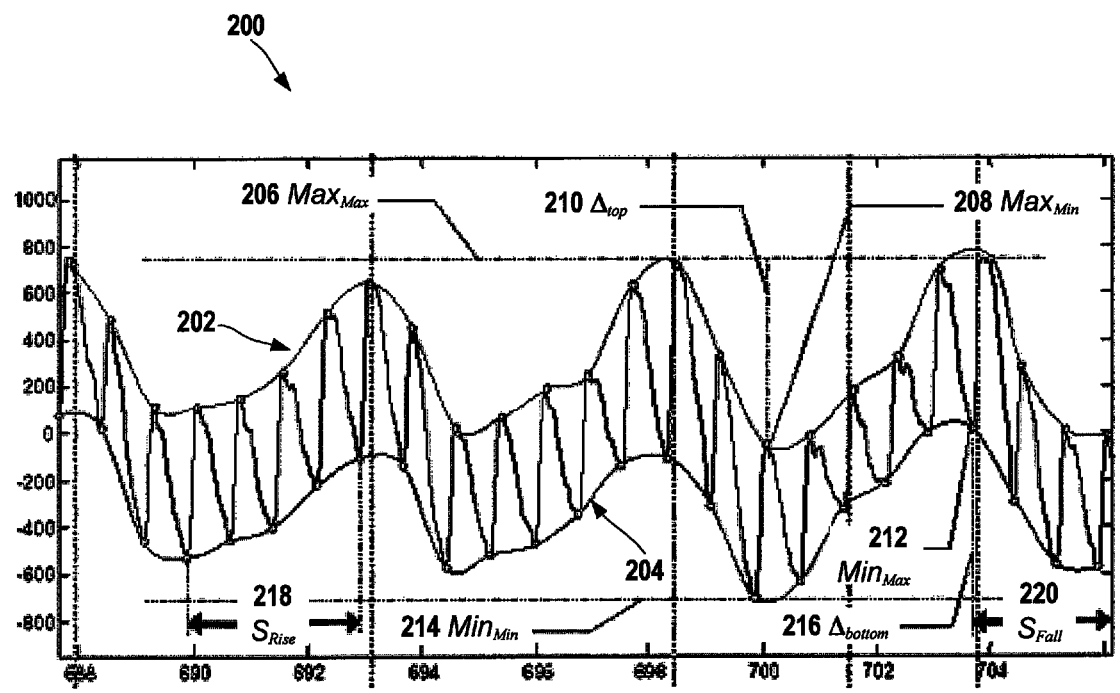
FIG. 2 shows Respiratory Induced Variation (RIV) features of a PPG.

FIG. 2 shows RIV features extracted from PPG data 200. Peaks and valleys of the cardiac components are marked with circles. The peaks are connected to form a top envelope 202, and the valleys are connected to form a bottom envelope 204. A maximum value of the top envelope, $Max_{Max}$ 206, is subtracted from a minimum value of the top envelope, $Max_{Min}$ 208, to determine a difference, $\Delta_{top}$ 210, in the height of the top envelope. Likewise, a maximum value of the bottom envelope, $Min_{Max}$ 212, is subtracted from a minimum value of the bottom envelope, $Min_{Min}$ 214, to determine a difference, $\Delta_{bottom}$ 216, in height of the bottom envelope. Periods where the top and bottom envelopes 202, 204 synchronously rise or fall are denoted as $S_{rise}$ 218 and $S_{fall}$ 220, respectively.

Two statistically robust metrics were developed to characterize the top and bottom envelopes 202, 204 of the PPG data 200. The first metric, $M_1$, detects when the height of the top envelope, $\Delta_{top}$ 210, is greater than the difference between the minimum of the top envelope, $\text{Max}_{Min}$, and the maximum of the bottom envelope, $\text{Min}_{Max}$. A sliding window of length $N_{m1}$, where $N_{m1}$ spans several respiratory cycles, is used to differentiate statistically relevant data from outliers. When $\Delta_{top} > (\text{Max}_{Min} - \text{Min}_{Max})$, a state of reduced blood volume is considered to be detected. The second metric, $M_2$, detects when the top and bottom envelopes 202, 204 synchronously rise or fall by a significant proportion of the peak amplitude over a window of sample length $Nm_2$. Because the PPG signal is inherently noisy, the metric must be robust and detect almost monotonic increases (decreases) in the envelope. This is done by sorting the $N_{m2}$ measurements from the envelope in ascending (descending) order. Then the Euclidean distance $d_{m2}$ is calculated between the sorted and unsorted data. The Euclidean distance between the two vectors is compared to the median peak height for the span. If the Euclidean distance is less than a predetermined percentage of the median, the data in the span are considered to be rising (falling) "almost" monotonically. The value of the predetermined percentage parameter is determined experimentally. If both the envelopes rise (fall) synchronously and the rise (fall) of the envelope is a significant proportion of the median peak height, a state of reduced blood volume is considered to be detected.

Example 1

Orthostatic Stress Tests and Detection of Baroreflex Response

A diverse group of eleven subjects, four women and seven men ages 20-43, participated in a study designed to simulate rapid blood loss. The only inclusion criterion was that subjects did not have a known cardiovascular condition.

Figure 3:
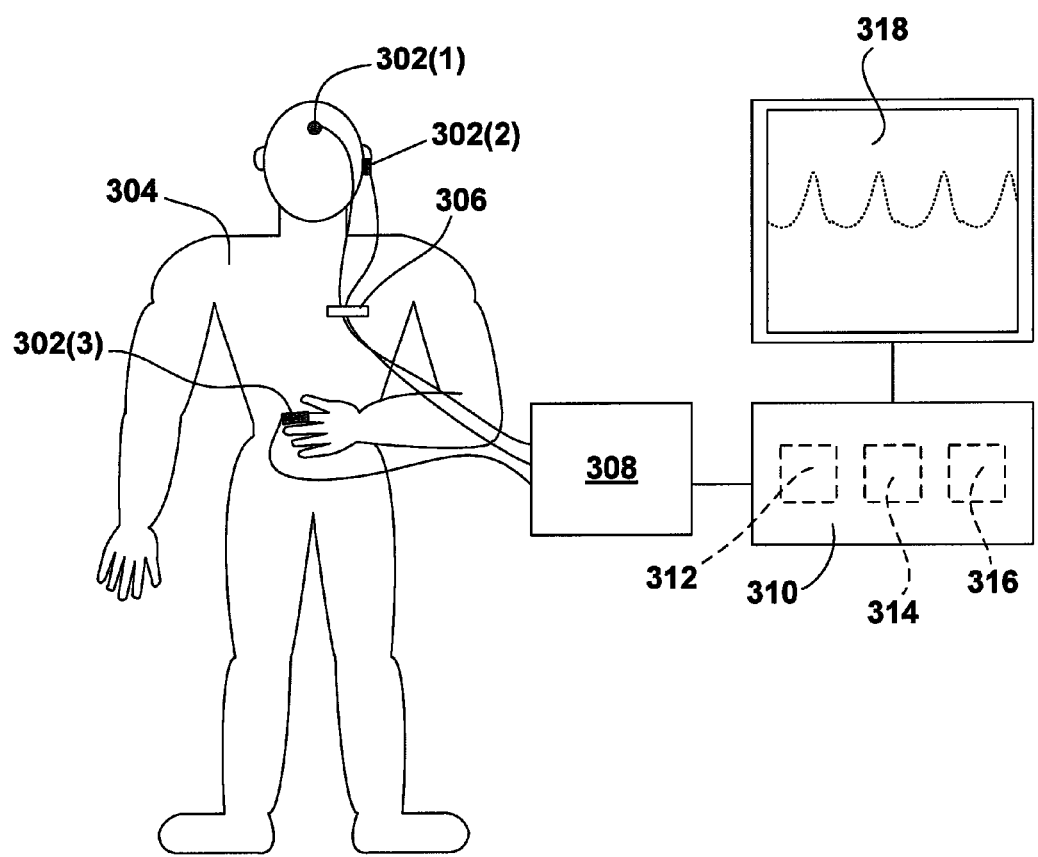
FIG. 3 is a block diagram of a system for detecting and quantifying baroreflex response in a human subject, according to an embodiment.

As shown in FIG. 3, three FDA-approved Nonin® (trademark of Nonin Medical, Inc., Plymouth, Minn.) pulse oximeter probes 302 were placed on each subject 304: a forehead reflectance probe 302(1) placed horizontally on the forehead and attached with a Nonin® holder; a reflective ear-clip sensor 302(2) placed on the left earlobe; and a transmission finger clip 302(3) placed on the left index finger. In order to prevent motion artifacts from cord movement and rotation, the cords from ear and forehead probes were tethered to the subject's shirt with a clip 306.

Each sensor was connected to a Nonin OEM III interface module 308 which generated data packets at 75 Hz of filtered 16-bit PPG data. The PPG signal was pre-processed by the OEM III with high pass and notch filters. A serial RS-232 interface allowed a personal computer 310 to record data. Personal computer 310 was equipped with a microprocessor 312, memory 314 and software 316. Data was observed on a display 318.

A Java-based program was developed to simultaneously log data from multiple sensors. The annotated data was saved by memory 314 in text files for later analysis.

In each trial, data was recorded continuously from the three pulse oximeter probes 302 for three minutes. The subjects 304 were instructed to breathe normally, remain still, not to talk and to keep their left hand in front of them, at their waist, during data collection. During the first minute, the subject 304 was supine on a couch. The subject was verbally prompted at fifty-seven seconds to prepare to stand and then prompted again at sixty seconds to stand. The subject remained stationary and standing for the next minute. The subject 304 was finally instructed to again recline on the couch for the final minute.

Figure 4:
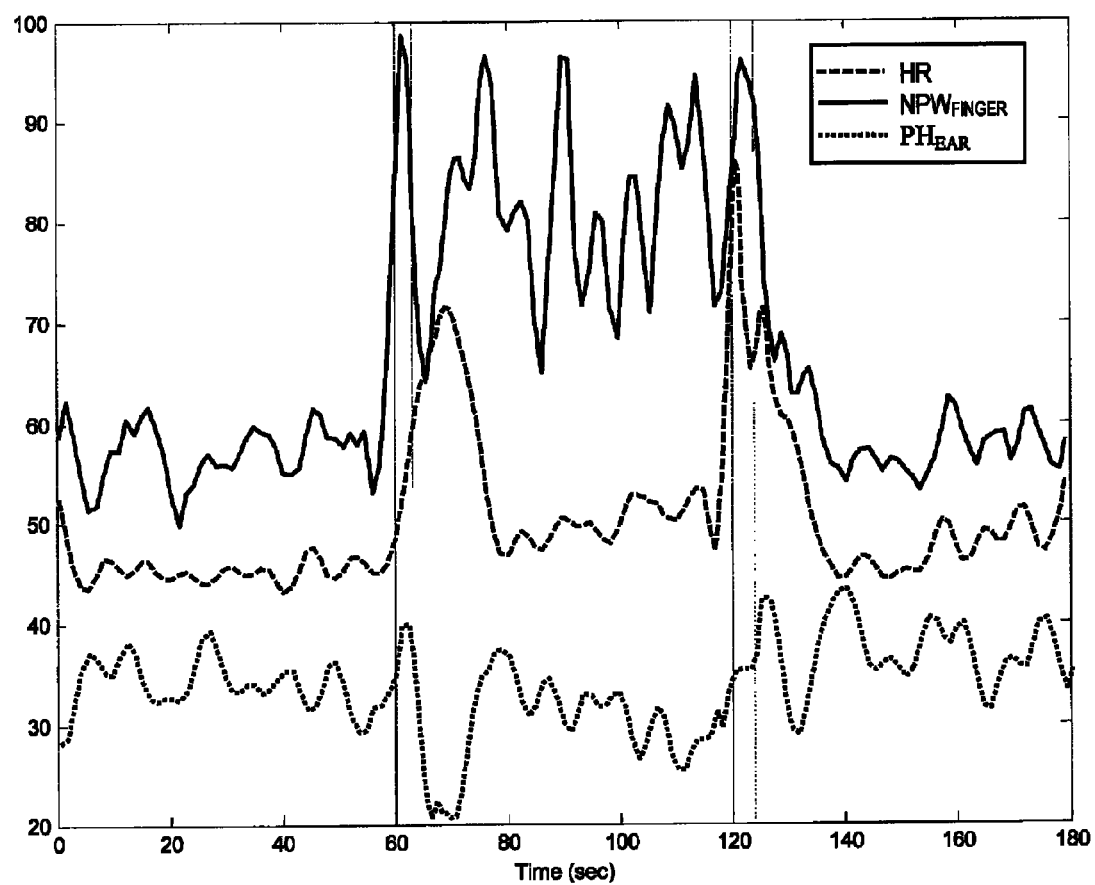
FIG. 4 shows filtered heart rate (HR), normalized peak width ($NPW_{Finger}$) and ear pulse height ($PH_{Ear}$) during an orthostatic stress test, according to an embodiment.

Matlab®-based signal processing software 316 was written to analyze the PPG data. The algorithm extracted pulse morphology features from the PPG using a mixed-state feature extractor based on previous work on sequential state estimation. See C. Schell, S. P. Linder et al. (2004) "Tracking highly maneuverable targets with unknown behavior" *Proceedings of the IEEE* 92(3): 558-574, which is incorporated herein by reference. This feature extractor allowed statistics of each individual pulse, including pulse height, width, area, rise and fall time, and instantaneous heart rate to be obtained as shown in FIG. 1. Changes in the morphology of individual pulses were analyzed and the data from the three sensors 302 were cross-correlated for each trial. FIG. 4 shows representative data from Subject 11, Trial 2, where it is observed that there is an abrupt increase in heart rate, pinching in the pulse amplitude of the ear PPG, and narrowing of the PPG peak upon standing. Standing and reclining at sixty and one-hundred twenty second are marked with vertical lines. In twenty-one of the thirty-three trials, the NPW begins to rise before the heart rate.

Derived PPG statistics were filtered using a Savitzky-Golay smoothing filter which fits a piecewise continuous polynomial spline to data. The Savitzky-Golay filter has the advantage of preserving sharp transitions. A window size of nine cardiac cycles, with a polynomial of order four, was used. The window size was selected to equal the length of a typical respiration cycle.

Events associated with standing were detected using a non-parametric single-tail Wilcoxon rank sum test. The Wilcoxon rank sum test was used instead of the commonly used Student's T-test because the PPG features cannot be parameterized as Gaussian. The Wilcoxon rank sum test was used to test the null hypothesis that one sample has a statistically significant probability of having a higher (or lower) median than another sample. The statistical threshold was $p<0.01$.

The event detector used a pair of consecutive sliding windows: $W_{baseline}$, a window used as a baseline consisting of the previous data; and $W_{event}$, a window of the most current data. An abrupt change in a feature, as would be caused by standing, was detected by testing if the median of the instantaneous data in $W_{event}$ was statistically different from the representative data in $W_{baseline}$. Because of RIV induced variations in the PPG statistics, the detection threshold was selected to maximize the probability of detection of standing for the thirty-three trials while minimizing the probability of false alarms from RIV induced variation in the PPG waveform.

Figure 5:
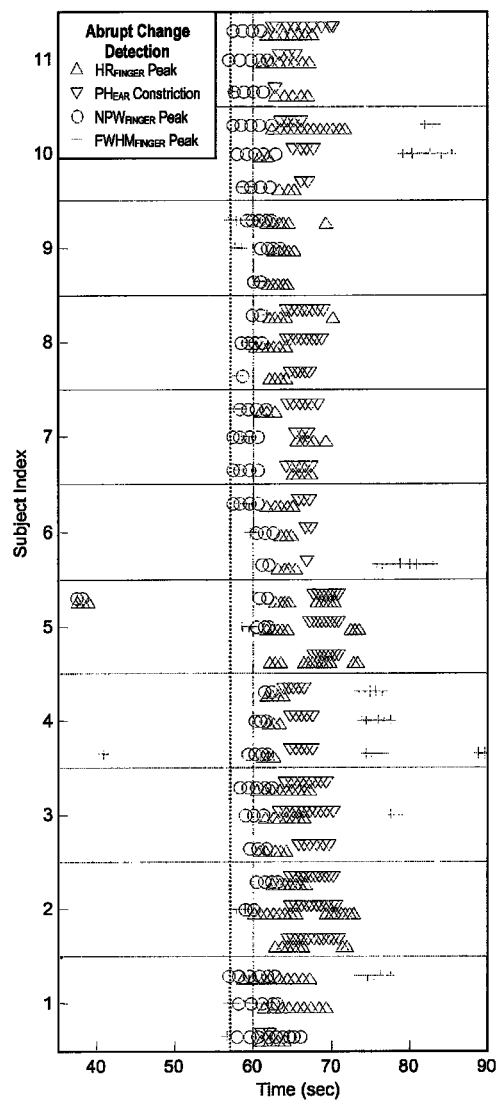
FIG. 5 shows output from real-time PPG detectors during an orthostatic stress test, according to an embodiment.

The output of real-time Wilcoxon-based detectors was tuned to discern abrupt increases in Heart Rate (HR), Full-Width Half Maximum (FWHM), and Normalized Peak Width (NPW) from the finger sensor, and abrupt decreases in ear Pulse Height from the ear sensor ($\text{PH}_{Ear}$). Two sensors were used because while the ear amplitude was suppressed it was not possible to accurately estimate the other three statistics. It was determined that the forehead PPG gave similar results to the finger PPG. As seen in FIG. 5, the detectors successfully detected standing while rejecting changes associated with a normal RIV. The vertical lines represent the three second prompt to stand and the start of standing at sixty seconds.

A peak in HR was detected by testing for a 20% increase in an instantaneous heart rate, defined as $W_{event}=5$ cardiac cycles, relative to a median pulse rate, defined as $W_{baseline}=40$ cardiac cycles. The constriction associated with standing was detected for nine of the eleven subjects with no false alarms. While Subject 1 has a visually detectable pinch, it was only detected for one trail. Subject 9 showed a unique response to standing, with the peak amplitude increasing for all three trials.

Figure 6:
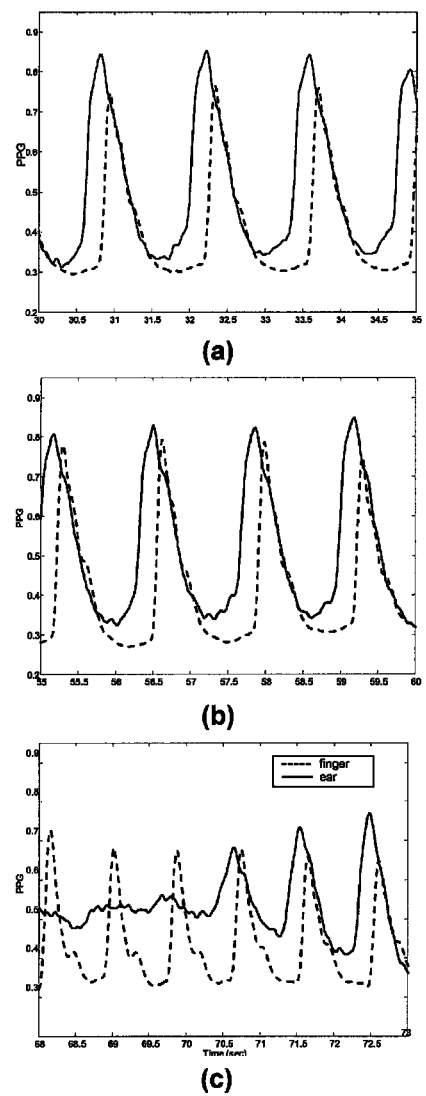
FIG. 6 shows changes in PPG waveforms during various phases of an orthostatic stress test, according to an embodiment.

A peak in the NPW corresponding to standing was detected by testing for a 5% increase in an instantaneous peak width, defined as $W_{event}=5$ cardiac cycles, relative to a median NPW, defined as $W_{baseline}=40$ cardiac cycles. Standing in all but two trials was detected; detection was missed for Subject 2, Trial 1, and Subject 5, Trial 1. One false positive was detected coincident with a false positive for HR. Visual inspection of FIG. 6 (representative data from Subject 11, Trial 1) shows that the peak becomes a comparatively wider portion of the cardiac period as the valley width decreases when subject is (a) supine, (b) preparing to stand, and (c) standing. The ear PPG is constricted at the start of standing.

Figure 7:
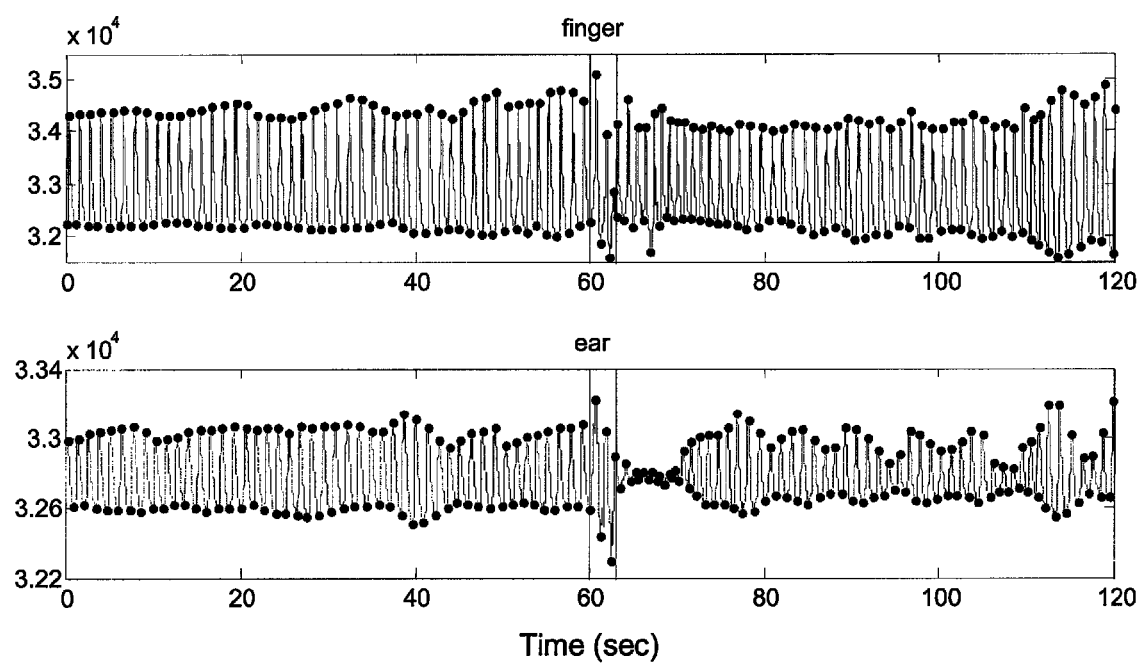
FIG. 7 shows PPG waveforms from finger and ear sensors during an orthostatic stress test, according to an embodiment.

A decrease in $PH_{Ear}$ corresponding to standing was detected by testing for a two-fold decrease in $PH_{Ear}$ relative to a median $PH_{Ear}$. A distinct change in PPG shape upon standing for the ear sensor can be seen in FIG. 7 (representative data from Subject 11, Trial 1), where dots mark the detected peaks and valleys of cardiac cycles and vertical lines mark the start and completion of standing.

Finally, standing was detected using FWHM by testing for a 5% increase (p<0.01), with a $W_{baseline}=40$ cardiac cycles and $W_{event}=5$ cardiac cycles. As seen in FIG. 5 these detections did not correlate well with standing, detecting standing in only 54% of the trials, with ten false positives. Visual inspection of the FWHM graphs showed that the half height width did not peak during standing for at least half of the subjects.

Example 2

Lower Body Negative Pressure Chamber Tests and Detection of Baroreflex Response

In a study designed to simulate moderate blood loss, two volunteers participated in three trials involving blood sequestration in the lower extremities using a lower body negative pressure (LBNP) chamber. The only inclusion criterion was that the subjects did not have a known cardiovascular condition. The subjects were awake, nonintubated and allowed to move, talk and breathe spontaneously.

The LBNP chamber located at the Institute of Surgical Research, Brooks Army Medical Center was used to produce a controlled orthostatic stress on each subject. Three FDA-approved Nonin® (trademark of Nonin Medical, Inc., Plymouth, Minn.) pulse oximeter probes 202 were placed on the subject's 204 finger and forehead. Data were collected and processed as described above.

In Trial 1, the pressure within the LBNP chamber was held for three minutes at each of the following negative pressures: 15, 30, 45 and 60 mmHg, successively. In Trial 2, the pressure within the LBNP chamber was held for five minutes at each of the following negative pressures: 15, 30, 45, 60, 70, 80 and 90 mmHg, successively. In Trial 3, the pressure within the LBNP chamber was reduced from atmospheric pressure (760 mmHg) to negative 80 mmHg over sixty seconds, and then held for nine minutes.

Figure 8:
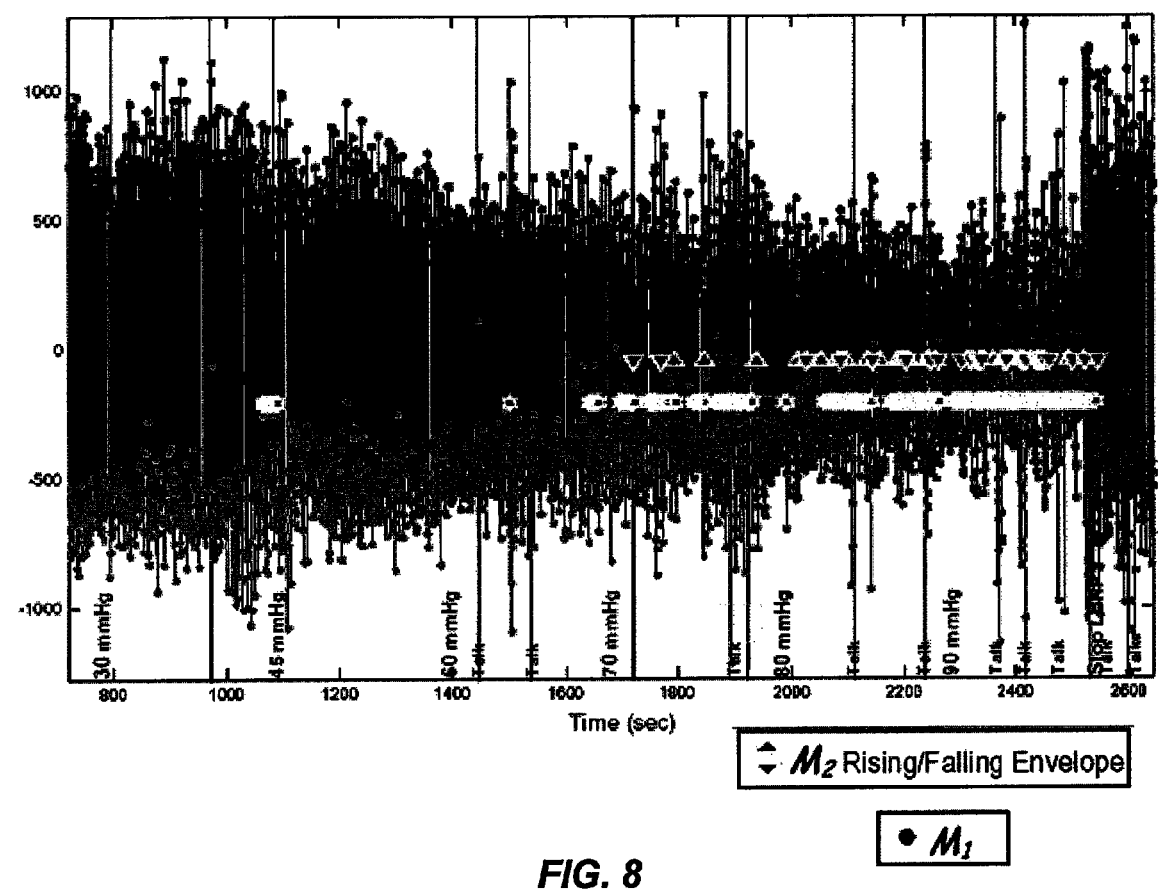
FIG. 8 shows output from a real-time PPG detector during a lower body negative pressure chamber test, according to an embodiment.
Figure 9:
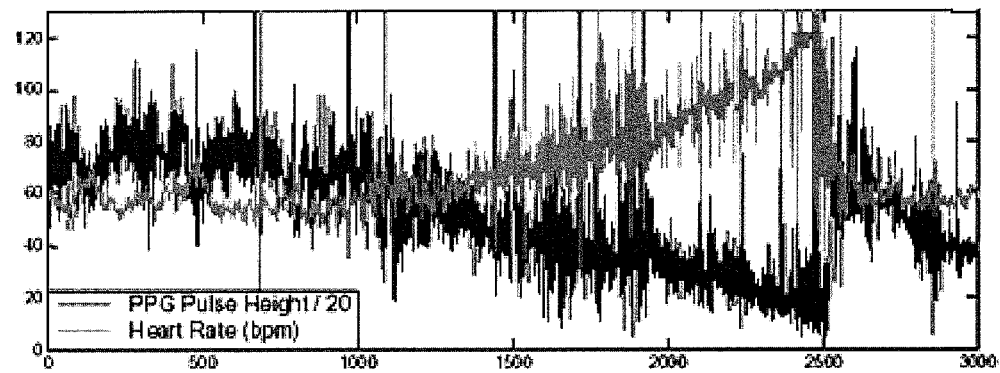
FIG. 9 shows PPG pulse height and heart rate obtained from the PPG data of FIG. 8.

Individual cardiac pulses were extracted and characterized for peak height, period and minimum and maximum values using Matlab®-based signal processing software. Markers were detected using metrics $M_1$ and $M_2$. Metric $M_1$ was used with a sliding window of width $N_{m1}=30$ cardiac cycles. As seen in FIG. 8, $M_1$ initially detects changes in the forehead PPG waveform when pressure within the LBNP chamber is set to negative 45 mmHg. Consistent detections occurred at pressures less than negative 70 mmHg. As seen in FIG. 9, these detections occurred before average heart rate rose about 80 bpm and PPG pulse height fell significantly. Similar results were obtained for Trial 3 where detections occurred at pressures less than negative 80 mmHg. Because Trial 1 had a maximum pressure of negative 60 mmHg, only intermittent detections were made.

Figure 10:
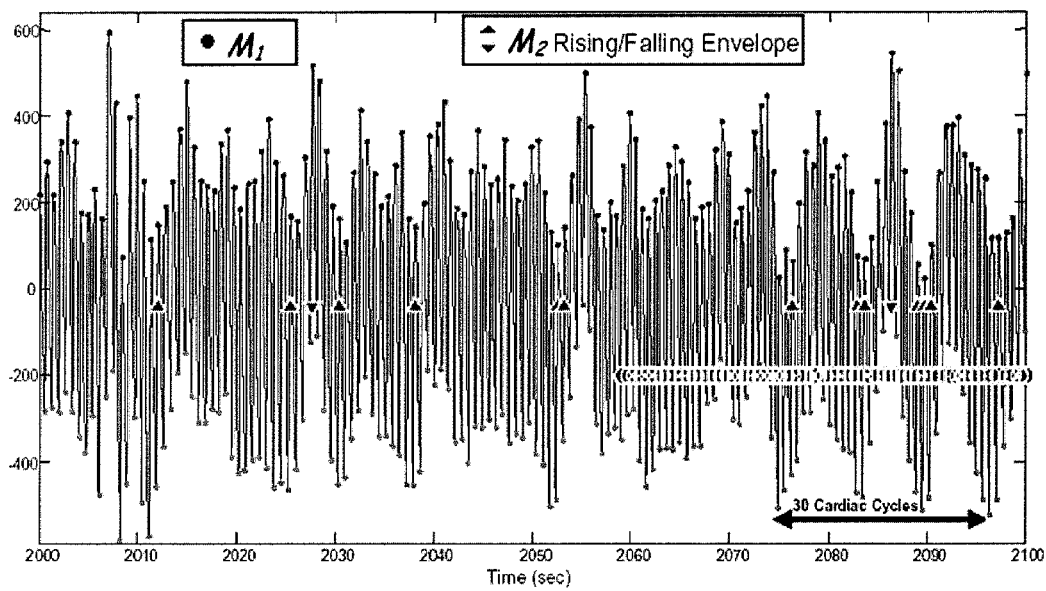
FIG. 10 shows an expanded view of a portion of PPG data from FIG. 8.

As shown in FIG. 10, which shows one hundred seconds of Trial 2, thirty cardiac cycles span approximately three respiratory cycles. During this time, $M_1$ is detected more frequently and more consistently than $M_2$. In one example of use, either $M_1$ or $M_2$ may be used alone to detect a state of reduced blood volume. In another example of use, accuracy may be improved when both $M_1$ and $M_2$ are detected.

Metric $M_2$ was used with a sliding window of width $N_{m2}=4$ cardiac cycles. The distance threshold $d_{m2}$ was set to 20-40% of the median peak height. FIG. 8 shows that $M_2$ detections from Trial 2 overlap with detections made using $M_1$. An upward pointing triangle indicates the detection of synchronously rising top and bottom envelopes, a downward pointing triangle indicates the detection of synchronously falling top and bottom envelopes. As seen in FIG. 10, detections using $M_2$ occurred when the envelope rose (or fell) synchronously, but the rising (falling) did not need to be monotonic.

Markers for decreased blood volume were consistently detected in the forehead, but the PPG data from the finger pulse oximeter showed a depressed respiratory component. Only during Trial 2 when the pressure was set to negative 90 mmHg were $M_1$ and $M_2$ detected in the finger PPG data.

Example 3

Detection of Exercise Induced Stress

In a study of exercise induced stress, nine subjects participated in a treadmill-based Bruce Protocol Stress Test to the point of volitional fatigue. All subjects were non-smokers, physically active, normotensive and screened for medications that would influence the results of the study. The experiments were approved by the Institutional Review Board of Dartmouth-Hitchcock Medical Center.

Three FDA-approved Nonin® (trademark of Nonin Medical, Inc., Plymouth, Minn.) pulse oximeter probes 202 were placed on the subject's 204 finger, ear and forehead. Data were collected at a rate of 300 Hz and processed as described above.

PPG spindle waves were detected using Matlab®-based signal processing software to analyze morphological features. For example, a spindle wave contains: (1) pinching of the cardiac cycle at both ends of the wave; (2) a smoothly rising and falling top envelope; (3) a smoothly rising and falling cardiac peak height; (4) a substantially symmetrical shape; (5) a minimum of five cardiac peaks; and (6) no outliers from motion artifacts.

Figure 11:
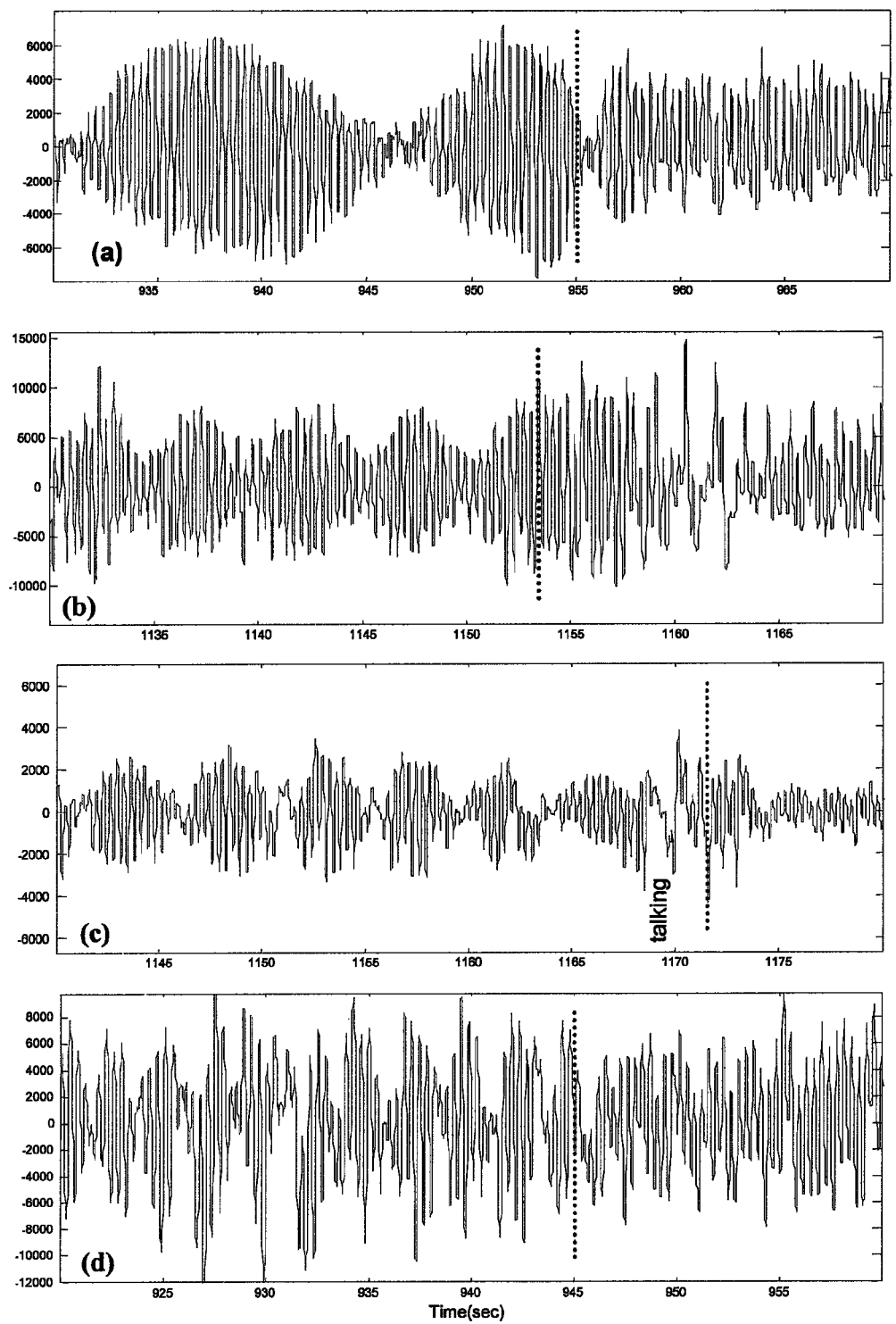
FIG. 11 shows PPG spindle waves from four subjects prior to volitional fatigue at the end of a Bruce Protocol Stress Test, according to an embodiment.
Figure 12:
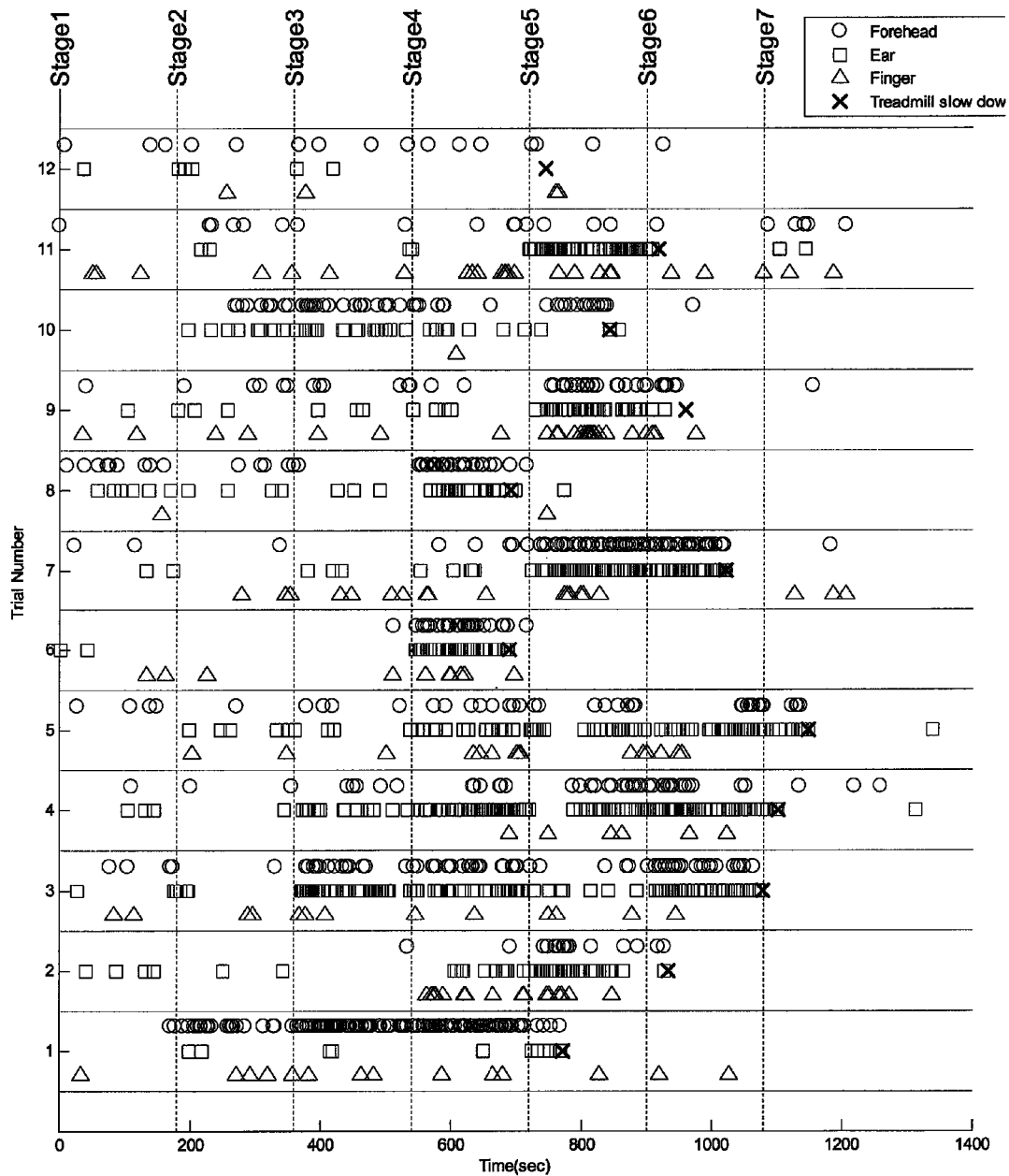
FIG. 12 shows output from real-time PPG detectors during a Bruce Protocol Stress Test, according to an embodiment.

All nine subjects completed the Bruce protocol with the following distribution of completed stages: Stage 4: 2; Stage 5: 1; Stage 6: 4; and Stage 7: 2. PPG spindle waves were detected in the forehead PPG of all nine subjects during the final stage before volitional fatigue, and with all subjects the spindle waves disappeared immediately when the treadmill was slowed to a walking pace. All subjects showed an increase in PPG amplitude as the trial progressed, with spindle waves becoming more pronounced after large increases. Shown in FIG. 11 are the PPG curves of four subjects with the time of volitional fatigue marked. FIG. 12 shows output from real-time PPG detectors during the Bruce Protocol Stress Test.

Figure 13:
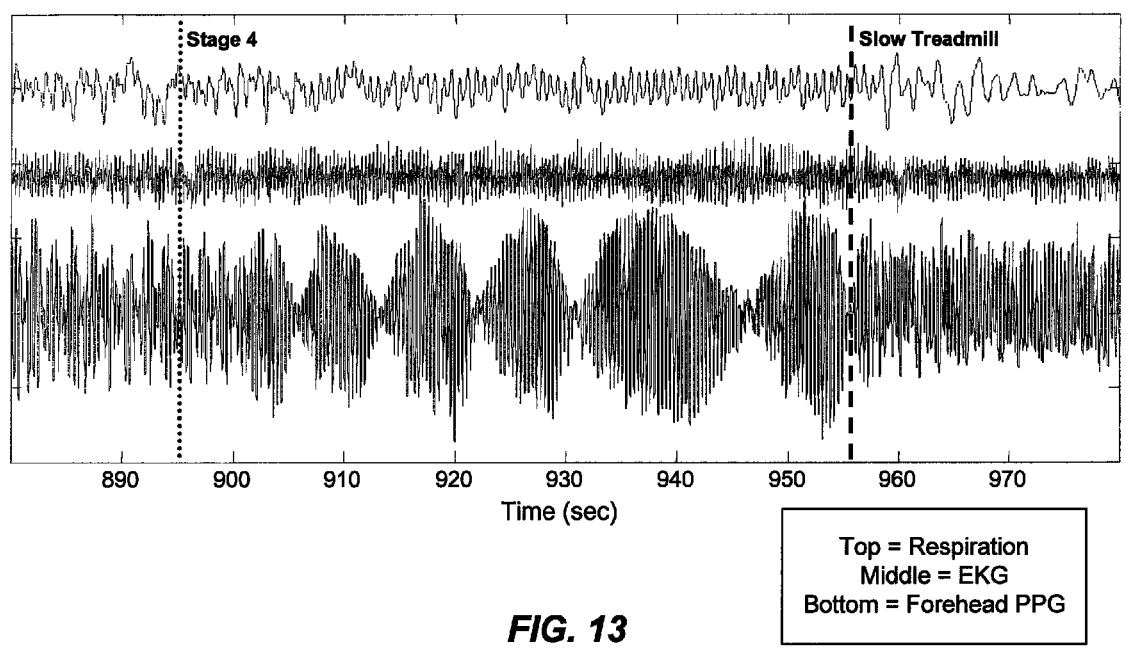
FIG. 13 shows a comparison of forehead PPG data, EKG data and respiratory data for a subject performing a Bruce Protocol Stress Test, according to an embodiment.

In seven of the nine subjects, spindle waves appeared before the final stage. Four subjects had spindle waves appear two stages before termination, and three had them appear one stage before. The period of the spindle waves shortened as the subjects became more fatigued, except for the subject shown in FIG. 13 where the spindles' periods lengthened after the final stage began. Spindle waves were detected in the ear PPG for seven subjects but in the finger PPG of only one subject.

Spindle waves were always of a longer period than respiration and EKG data showing that the heart beat normally when the PPG amplitude pinched. As an example, Subject 1, shown in FIG. 13 has a respiration of 60 breaths/min and a steady heart rate 168 bpm. As with all subjects, when she approached her maximum heart rate, the variability in heart rate disappeared.

It is hypothesized that the formation of spindle waves relates to periodic pinching of blood flow to the skin, as a mechanism to increase cerebral blood flow, when other mechanisms are unavailable, e.g., during exercise-induced stress when the heart rate cannot be easily increased, and the skin is vasodilated to shed heat.

Figure 14:
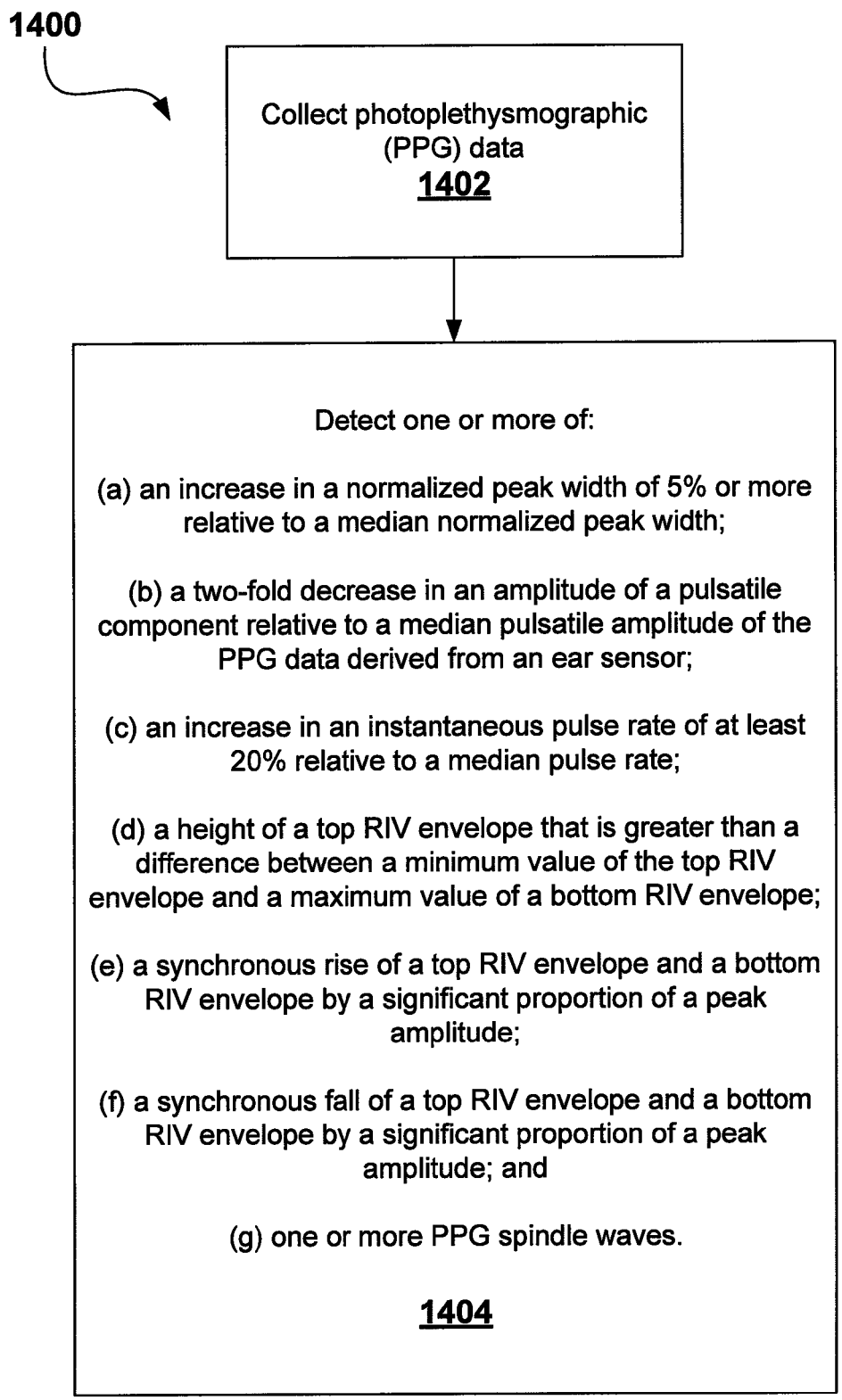
FIG. 14 shows a flowchart illustrating one process for observing baroreflex response using a pulse oximeter, according to an embodiment.

FIG. 14 shows a flowchart illustrating one process 1400 for observing baroreflex response using a pulse oximeter. In step 1402, PPG data 100, 200 is collected. In step 1404, one or more of the following is detected: (a) an increase in a normalized peak width of 5% or more relative to a median normalized peak width; (b) a two-fold decrease in an amplitude of a pulsatile component relative to a median pulsatile amplitude of the PPG data derived from an ear sensor; (c) an increase in an instantaneous pulse rate of at least 20% relative to a median pulse rate; (d) a height of a top RIV envelope that is greater than a difference between a minimum value of the top RIV envelope and a maximum value of a bottom RIV envelope; (e) a synchronous rise of a top RIV envelope and a bottom RIV envelope by a significant proportion of a peak amplitude; (f) a synchronous fall of a top RIV envelope and a bottom RIV envelope by a significant proportion of a peak amplitude; and (g) a PPG spindle wave.

The changes described above, and others, may be made in the systems and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. A software product comprising instructions, stored on non-transitory computer-readable media, wherein a computer executes the instructions- to perform steps for detecting the presence of a baroreflex response, comprising:
   instructions for obtaining photoplethysmographic (PPG) data;
   instructions for determining a normalized peak width of each cardiac cycle from the PPG data;
   instructions for determining a median normalized peak width using a representative sample of cardiac cycles derived from the PPG data; and
   instructions for providing a result indicative of the presence of the baroreflex response when a statistically significant increase in the normalized peak width relative to the median normalized peak width is detected;
   wherein the statistically significant increase is detected using a statistical threshold of $p<0.01$.

2. The software product of claim 1, further comprising instructions for providing a result indicative of the absence of detection of the baroreflex response when the statistically significant increase in the normalized peak width relative to the median normalized peak width is not detected.

3. The software product of claim 1, wherein the PPG data is derived from an ear sensor, and further comprising:
   instructions for determining an amplitude of the pulsatile component of each cardiac cycle in the PPG data;
   instructions for determining a median pulsatile amplitude using the representative sample of cardiac cycles derived from the PPG data; and
   instructions for providing a result indicative of the presence of the baroreflex response when a statistically significant decrease in the amplitude of the pulsatile component relative to the median pulsatile amplitude is detected: the statistically significant decrease being detected using a statistical threshold of $p<0.01$.

4. The software product of claim 3, further comprising instructions for providing a result indicative of the absence of detection of the baroreflex response when:
   the statistically significant decrease in the amplitude of the pulsatile component relative to the median pulsatile amplitude is not detected, and
   the statistically significant increase in the normalized peak width relative to the median normalized peak width is not detected, using the statistical threshold of $p<0.01$.

5. The software product of claim 1, further comprising:
   instructions for determining an instantaneous pulse rate;
   instructions for determining a median pulse rate using the representative sample of cardiac cycles derived from the PPG data; and
   instructions for providing a result indicative of the presence of the baroreflex response when a statistically significant increase in the instantaneous pulse rate relative to the median pulse rate is detected using a statistical threshold of $p<0.01$.

6. The software product of claim 5, further comprising instructions for providing a result indicative of the absence of detection of the baroreflex response when:
   the statistically significant increase in the instantaneous pulse rate relative to the median pulse rate is not detected, and
   the statistically significant increase in the normalized peak width relative to the median normalized peak width is not detected.

7. The software product of claim 1, further comprising instructions for recording and saving data to memory.

8. A software product comprising instructions, stored on non-transitory computer-readable media, wherein a computer executes the instructions to perform steps for detecting the presence of a baroreflex response, comprising:
   instructions for obtaining photoplethysmographic (PPG) data;
   instructions for determining two or more of the following parameters:
      (a) a normalized peak width of each cardiac cycle;
      (b) an amplitude of the pulsatile component of each cardiac cycle in the PPG data derived from an ear sensor or a forehead sensor; and
      (c) an instantaneous pulse rate;
   instructions for determining a median value for the two or more parameters using a representative sample of cardiac cycles; and
   instructions for providing a result indicative of the presence of the baroreflex response when statistically significant changes in the median values are detected using a statistical threshold of $p<0.01$; the statistically significant changes being: when the normalized peak width is determined, a statistically significant increase in the median peak width; when the instantaneous pulse rate is detected, a statistically significant increase in the median pulse rate; and when the amplitude of the pulsatile component is detected, a statistically significant decrease in the median amplitude.

* * * * *